(12) United States Patent
Lee et al.

(10) Patent No.: US 8,466,103 B2
(45) Date of Patent: Jun. 18, 2013

(54) EXENDIN POLYPEPTIDE LINKED TO BIOTIN, METHOD FOR THE PREPARATION THEREOF AND PHARMACEUTICAL COMPOSITION COMPRISING THE SAME

(75) Inventors: Kang Choon Lee, Seoul (KR); Su Young Chae, Seoul (KR); Cheng Hao Jin, Suwon (KR)

(73) Assignee: B&L Delipharm, Corp., Suwon, Gyeonggi-Do (KR)

( * ) Notice: Subject to any disclaimer, the term of this patent is extended or adjusted under 35 U.S.C. 154(b) by 18 days.

(21) Appl. No.: 12/919,399

(22) PCT Filed: May 14, 2008

(86) PCT No.: PCT/KR2008/002694
§ 371 (c)(1),
(2), (4) Date: Aug. 25, 2010

(87) PCT Pub. No.: WO2009/107900
PCT Pub. Date: Sep. 3, 2009

(65) Prior Publication Data
US 2011/0257084 A1    Oct. 20, 2011

(30) Foreign Application Priority Data

Feb. 25, 2008 (KR) .................. 10-2008-0016833

(51) Int. Cl.
| A61K 38/17 | (2006.01) |
| A61P 3/04 | (2006.01) |
| A61P 3/10 | (2006.01) |
| A61P 1/00 | (2006.01) |
| C07K 14/46 | (2006.01) |
| C07K 1/14 | (2006.01) |

(52) U.S. Cl.
USPC ............. 514/6.9; 514/4.8; 514/6.8; 514/21.3; 530/324

(58) Field of Classification Search
None
See application file for complete search history.

(56) References Cited

U.S. PATENT DOCUMENTS

| 5,424,286 A | 6/1995 | Eng | |
| 5,766,897 A * | 6/1998 | Braxton | 435/463 |
| 6,924,264 B1 * | 8/2005 | Prickett et al. | 514/6.9 |
| 7,329,646 B2 * | 2/2008 | Sun et al. | 514/6.7 |

FOREIGN PATENT DOCUMENTS

KR    10-0746658 B1    7/2007

OTHER PUBLICATIONS

Kolchanov, 1988, Journal of Molecular Evolution, vol. 27, pp. 154-162.*
Pasquo, 2012, PLoS One, vol. 7, Issue 2, e32555.*
Larsen et al., "Systemic administration of the long-acting GLP-1 derivative NN2211 induces lasting and reversible weight loss in both normal and obese rats," Diabetes, 50(11):2530-9 (Nov. 2001).
Shechter et al., "[2-Sulfo-9-flourenylmethoxycarbonyl]-exendin-4-a long-acting glucose-lowering prodrug", Biochem Biophys Res Commun., 305(2):386-91 (May 30, 2003).
International Search Report for PCT/KR2008/002694, mailed Nov. 27, 2008.

* cited by examiner

Primary Examiner — Robert Landsman
Assistant Examiner — Ian Dang
(74) Attorney, Agent, or Firm — Edwards Wildman Palmer LLP

(57) ABSTRACT

Disclosed are exendin-3 or exendin-4 derivatives modified with biotin, a preparation method thereof and a pharmaceutical composition containing the same. More specifically, disclosed are exendin-3 or exendin-4 derivatives in which the lysine residue of exedin is modified with biotin. The disclosed exendin-3 or exendin-4 derivatives modified with biotin show biological activity similar to that of native exendin and at the same time, have increased in vivo stability and are easily absorbed through the mucosa. Thus, biotin-modified exendin-3 or exendin-4 derivatives are useful for treating diseases, which can be caused by the excessive secretion of insulin, the lowering of plasma glucose, the inhibition of gastric or intestinal motility, the inhibition of gastric or intestinal emptying or the inhibition of food intake. Particularly, the biotin-modified exendin-3 or exendin-4 derivatives are useful for the treatment of diabetes, obesity and irritable bowel syndromes.

15 Claims, 9 Drawing Sheets

EXENDIN POLYPEPTIDE LINKED TO BIOTIN, METHOD FOR THE PREPARATION THEREOF AND PHARMACEUTICAL COMPOSITION COMPRISING THE SAME

CROSS-REFERENCES TO RELATED APPLICATIONS

This application is a U.S. national phase application, pursuant to 35 U.S.C. §371 of PCT/KR2008/002694, filed May 14, 2008, designating the United States, which claims priority to Korean Application No. 10-2008-0016833, filed Feb. 25, 2008. The entire contents of the aforementioned patent applications are incorporated herein by this reference.

TECHNICAL FIELD

The present invention relates to exendin-3 or exendin-4 derivatives modified with biotin or its conjugate, a preparation method thereof and a pharmaceutical composition containing the same.

BACKGROUND ART

Glucagon-like peptide-1 (hereinafter to be referred to as "GLP-1") induces numerous biological effects such as stimulating insulin secretion, inhibiting glucagon secretion, inhibiting gastric emptying, inhibiting gastric motility or intestinal motility, enhancing glucose utilization, and inducing weight loss. It is known that GLP-I may further act to prevent the pancreatic β-cell deterioration that occurs as type II diabetes, non-insulin dependent diabetes mellitus (NIDDM), progresses, and to recover insulin secretion by stimulating the production of new β-cells. Particularly, a significant characteristic of GLP-1 is its ability to stimulate insulin secretion without the associated risk of hypoglycemia that is seen when using insulin therapy or some types of oral therapies that act by increasing insulin expression. In addition, GLP-I is very effective in the treatment of type II diabetes because it does not involve side effects, such as the apoptosis and necrosis of pancreatic β-cells, which result from the long-term administration of the blood glucose-lowering drug sulfonylurea and the like.

However, the usefulness of therapy involving GLP-1 peptides has been limited by the fact that GLP-1 is poorly active, and the two naturally occurring truncated peptides, GLP-1(7-37)OH and GLP-1(7-36)NH$_2$, are rapidly cleared in vivo and have extremely short in vivo half lives. Particularly, it is known that endogenously produced dipeptidyl-peptidase IV (hereinafter to be referred to as "DPP-IV") inactivates circulating GLP-1 peptides by removing the N-terminal histidine (7) and alanine (8) residues and is a major reason for the short in vivo half-life [see O' Harte et al., 2000].

For this reason, various approaches have been attempted either to use DPP-IV inhibitors (P93/01, NVP-LAF237, NVP-DPP728, 815541A, 823093, MK-0431, etc.) to inhibit the degradation of GLP-1, or to use GLP-1 receptor agonists or GLP-1 derivatives (exendin, liraglutide, GLP-1/CJC-1131, etc.) to extend the half life of GLP-1 peptides while maintaining the biological activity or reduce the rate of the removal of GLP-1 peptides from the body.

Also, exendins, another group of peptides that lower blood glucose levels, were suggested for the first time by John Eng (see U.S. Pat. No. 5,424,286, exendin-3 [SEQ ID NO: 1] HSDGTFTSDL SKQMEEEAVR LFIEWLKNGG PSSGAPPPS and exendin-4). Exendin-4 has the following sequence and shows partial sequence similarity (53%) to GLP-1(7-36)NH$_2$ [see Goke et al., 1993].

His $^1$-Gly-Glu-Gly-The-Phe-The-Ser-Asp-Leu-Ser-Lys $^{12}$-Gln-Met-Glu-Glu-Glu-Ala-Val-Arg-Leu-Phe-Ile-Glu-Trp-Leu-Lys$^{27}$-Asn-Gly-Gly-Pro-Ser-Ser-Gly-Ala-Pro-Pro-Pro-Ser-NH$_2$ (SEQ ID NO: 2: HGEGTFTSDL SKQMEEEAVR LFIEWLKNGG PSSGAPPPS).

Meanwhile, the exendins are blind in the venom of Helodermatidae or beaded lizards. Exendin-3 is present in the venom of *Heloderma horridum*, the Mexican beaded lizard, and exendin-4 is present in the venom of *Heloderma suspectum*, the Gila monster. Also, exendin-4 differs from exendin-3 at only positions two and three. It has resistance to degradation by DPP-IV in mammals and has a longer half-life than GLP-1 having a half-life of less than 2 minutes for DPP-IV [see Kieffer T J et al., 1995]. The results of in vivo experiments revealed that exendin-4 shows a half-life of 2-4 hours and can reach a sufficient blood level when it is intraperitoneally administered 2-3 times a day [see Fineman M S et al., 2003]. Also, exendin-4 is known to regulate gastric motility, reduce food intake and inhibit plasma glucagon (U.S. Pat. Nos. 6,858,576, 6,956,026 and 6,872,700). With respect to the blood glucose-regulating action of exendin-4, it was reported that, when exendin-4 was administered alone or in combination with an antidiabetic agent (such as sulfonylurea or metformin) far 28 days, it lowered the level of glycosylated hemoglobin (HbA1C) (which means the amount of hemoglobin bound to glucose in blood) to less than 1% [see Egan J M et al., 2003]. Recently, synthetic exendin-4 (commercially available under the trade name of Byetta™) was approved for use by the US FDA.

Meanwhile, vitamins, which are essential nutrients necessary for a variety of biological processes, are involved directly in human metabolism and growth, particularly the production of digestive enzymes, antibodies and fatty acids, and when they are deficient, various diseases occur. However, for humans and mammals, it is necessary to obtain such vitamins from external sources because they have no ability to synthesize vitamins. For this reason, transport systems capable of absorbing such vitamins are very well developed in the human small intestine, and such vitamins are absorbed into various intestinal sites of the human body through a active transport system, a concentration-dependent passive transport system, an intracellular transport system, a receptor-mediated endocytotic pathway or the like depending on various environmental conditions such as concentration or pH. For example, thiamin and niacin are mostly absorbed in the duodenum, and cyanocobalamin is absorbed throughout the small intestines. They have specific transport systems, the most well-known system of which is a Na-dependent multivitamin transport system, which is a biotin transport system, a kind of active transport system. This system is known to be distributed equally in various human organs, such as liver, kidneys or heart, in addition to small intestines. The affinity constant of this system for biotin in small intestines is known to be about 2.6 nM.

Accordingly, the present inventors have conducted studies to develop exendin derivatives specifically modified with biotin at a specific position of exendin, which are highly pure, increase the in vivo residence time of exendin, are easily absorbed through the mucosa and have the pharmacokinetic profiles and pharmacological properties similar to the therapeutic effects of native exendin by injection, as well as a preparation method thereof and a pharmaceutical composition containing the same.

DISCLOSURE OF INVENTION

Technical Problem

It is an object of the present invention to provide exendin derivatives modified with biotin.

Another object of the present invention is to provide exendin-3 or exendin-4 derivatives modified with biotin.

Still another object of the present invention is to provide a method for preparing said exendin-3 or exendin-4 derivatives modified with biotin.

Yet another object of the present invention is to provide a pharmaceutical composition containing said exendin-3 or exendin-4 derivatives modified with biotin.

Technical Solution

To achieve the above objects, the present invention provides: 1) exendin derivatives modified with biotin; and 2) a composition for preventing or treating diseases, which are caused by the excessive secretion of insulin, the lowering of plasma glucose, the inhibition of gastric or intestinal motility, the inhibition of gastric or intestinal emptying or the inhibition of food intake, the composition containing said biotin-modified exendin derivatives as active ingredients.

Hereinafter, the present invention will be described in detail.

In one aspect, the present invention provides biotin-modified exendin derivatives or pharmaceutically acceptable salts thereof.

The exendin that is modified according to the present invention may be native exendin or recombinant exendin, and is preferably exendin-3 or exendin-4.

Also, the exendin derivative modified with exendin according to the present invention may be a form in which exendin-4 is modified with biotin at lysine 12 ($Lys^{12}$-mono-biotin-exendin-4; hereinafter to be referred to as "MB1-exendin-4", a form in which exendin-4 is modified with biotin at lysine 27 ($Lys^{27}$-mono-biotin-exendin-4; hereinafter to be referred to as "MB2-exendin-4"), or a form in which exendin-4 are modified with biotin at lysines 12 and 27 ($Lys^{12, 27}$-di-biotin-exendin-4; hereinafter to be referred to as "DB-exendin-4". The most preferred is the form in which exendin-4 is modified with biotin at lysines 12 and 27.

In another aspect, the present invention provides a method for preparing said biotin-modified exendin derivatives, the method comprising the steps of: (1) adding biotin, exendin and a reducing agent to a buffer solution or an organic solvent and allowing the mixture to react; (2) storing the reaction mixture of step (1) at a given temperature for a given time in a light-shielded condition; (3) removing unreacted reactants from the reaction mixture of step (2); and (4) separating and purifying biotin-modified exendin from the product of step (3), from which the unreacted reactants have been removed.

In step (1) of the method according to the present invention, the reaction molar ratio of biotin to exendin is preferably selected in the range of 1-4. The selection of the reaction molar ratio can be performed in consideration of the molecular structure and molecular weight of biotin, the pH of the reaction solution, reaction temperature, reaction time, etc.

Said buffer solution or organic solvent is not specifically limited, and a buffer solution, which is conventionally used in the art, can be suitably selected depending on biotin which is used for the modification of exendin.

The storage temperature and time in step (2) of the method according to the present invention are preferably suitably adjusted depending on biotin used in the modification of exendin, as described above with respect to the reaction molar ratio. For example, the reaction mixture may be stored at 4° C. for 6 hours or at room temperature for a shorter time. The storage temperature and time are connected with the reactivity of biotin used for the modification of exendin. During the storage step, the modification reaction is carried out, and after the passage of a suitable amount of time, the modification reaction can be stopped using a glycine solution or a trifluoroacetic acid solution.

The removal of unreacted reactants in step (3) of the inventive method can be performed through a method which is conventionally used in the art. For example, the unreacted reactants may be removed by dialysis using a suitable buffer solution, such as PBS (phosphate buffered saline).

The separation and purification in step (4) of the inventive method can be performed, but not limited to, using size-exclusion chromatography, reverse-phase high-performance liquid chromatography, etc.

In still another aspect, the present invention provides a composition for preventing or treating diseases which are caused by the excessive secretion of insulin, the lowering of plasma glucose, the inhibition of gastric or intestinal motility, the inhibition of gastric or intestinal emptying or the inhibition of food intake, the composition comprising said biotin-modified exendin derivatives as active ingredients.

The inventive composition containing the biotin-modified exendin derivatives as active ingredients may be formulated into a variety of oral or parenteral dosage forms far clinical administration, but the scope of the present invention is not limited thereto.

The inventive composition may be formulated using conventional diluents or excipients, such as fillers, extenders, binders, wetting agents, disintegrants, surfactants and the like. Solid preparations for oral administration include tablets, pills, powders, granules, capsules, etc. These solid preparations are formulated by mixing the inventive composition with at least one excipient, for example, starch, calcium carbonate, sucrose, lactose or gelatin.

In addition to simple excipients, lubricants such as magnesium stearate or talc are also used. Liquid preparations for oral administration include suspensions, solutions, emulsions, syrups, etc., and may include commonly used, simple diluents such as water and liquid paraffin, and if desired, may further include various excipients, for example, wetting agents, sweeteners, aromatics and preservatives. Preparations for parental administration include sterile aqueous solutions, non-aqueous solutions, suspensions, emulsions, freeze-dried preparations, suppositories, etc. For non-aqueous solutions and suspensions, propylene glycol, polyethylene glycol, vegetable oils such as olive oil, and injectable esters such as ethyloleate may be used. In addition, calcium or vitamin $D_3$ may be added to the inventive composition to enhance the effect of treating proliferative diseases or autoimmune diseases.

The dosage of the inventive composition may vary depending on the patient's weight, age, sex, general health conditions, diet, administration time, administration route, excretion rate and disease severity, but an effective dosage of the composition may be administered several times for 1-2 weeks. In addition, the composition may be administered once or several times within a daily effective dosage range.

Advantageous Effects

The exendin modified with biotin according to the present invention can have an increased in vivo half-life and show a biological activity similar to that of native exendin. Also, by selectively limiting the position of conjugation and the number of conjugations, side effects resulting from such factors can be minimized. In addition, the exendin-3 or exendin-4 derivatives modified with biotin according to the present invention are useful for preventing and treating diseases such as diabetes or obesity, which are caused by the excessive secretion of insulin, or diseases such as irritable bowel syndromes, which are caused by the lowering of plasma glucose, the inhibition of gastric or intestinal mobility, the inhibition of gastric or intestinal emptying or the inhibition of food intake.

MODE FOR THE INVENTION

Figure 1:
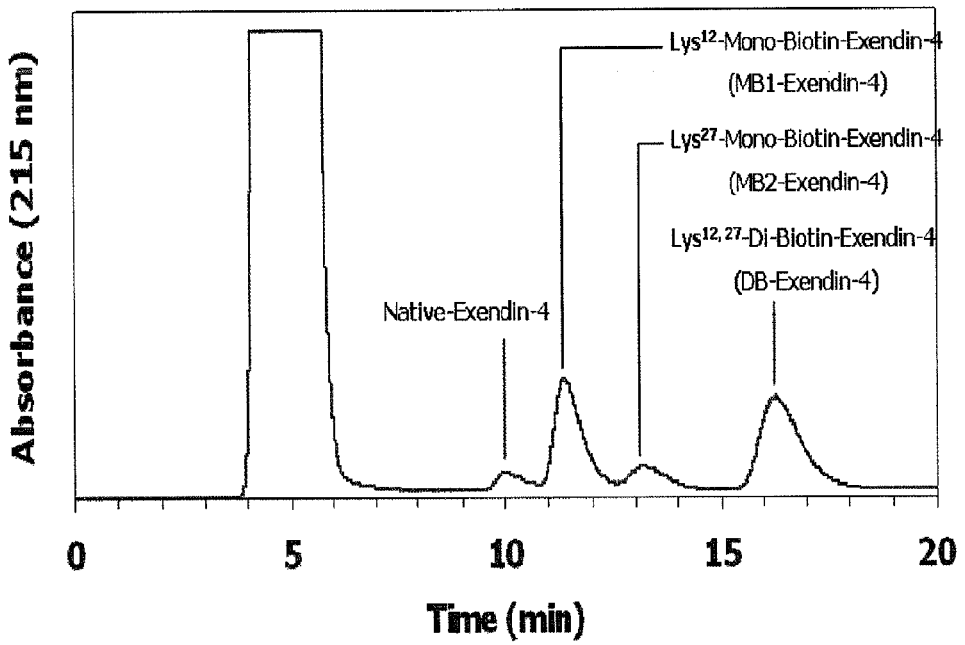
FIG. 1 shows an HPLC chromatogram of a mixture of exendin-4, $Lys^{12}$-Mono-Biotin-Exendin-4 (hereinafter referred to as "MB1-Exendin-4), $Lys^{27}$-Mono-Biotin-Exendin-4 (hereinafter referred to as MB2-Exendin-4) and $Lys^{12, 27}$-Di-Biotin-Exendin-4 (hereinafter referred to as DB-Exendin-4) according to the present invention.

Hereinafter, the present invention will be described in further detail with reference to examples. It is to be understood, however, that these examples are illustrative only, and the scope of the present invention is not limited thereto.

EXAMPLES

Example 1

Preparation of Exendin-3 or Exendin-4 Derivatives Modified with Biotin

100 μl of triethylamine (TEA) (Sigma, 9% TEA-containing DMSO solution) was added to 100 μl of exendin-3 or exendin-4 (Bachem, 10 mg/ml in 0.3% TEA-containing DMSO solution), and then 100 μl of biotin-NHS (Sigma, 0.8 mg/ml in 0.3% TEA-containing DMSO solution) was added thereto and well stirred. The molar ratio of exendin-3 or exendin-4 to Biotin-NHS was 1:2, and the mixture was allowed to react at room temperature for 60 minutes. The reaction was stopped with 300 μl of 1% trifluoroacetic acid (TFA)-containing distilled water.

Example 2

Separation, Purification and Analysis of Exendin-3 or Exendin-4 Derivatives Modified with Biotin The exendin-4 derivatives, prepared in Example 1, were separated using reverse-phase high-performance liquid chromatography (hereinafter referred to as "RP-HPLC"). As columns, Jupiter RP-18 (250×10 mm, 5 Phenomenex, USA) and Capcell-pak RP-18 (250×4 mm, 5 μm, Shiseido, Japan) were used, and as mobile phase solvents, 36-41% solvent B (0.1% TFA-containing acetonitrile) and 64-59% solvent A (0.1% TFA-containing distilled water) were used. The mobile phase was linearly changed while maintaining a flow rate of 1 ml/min. Each peak was quantified using a UV spectrophotometer at 215 nm. The biotin-modified exendin-3 or exendin-4 derivatives, prepared through the above-described method, were analyzed with a MALDI-TOF mass spectrometer to determine the number of biotin conjugates. Also, the derivatives were digested with the protease lysine-C, and then analyzed with a MALDI-TOF mass spectrometer. Each of the purified conjugates was dissolved in 50 μl of triethylamine-HCl buffer (10 mmol/L; pH 7.4) at a concentration of 1 mg/ml, and then 50 μl of an enzyme (1 mg/ml) was added thereto and allowed to react at 37° C. for 1 hour. 5 μl of 10% (ẇ) TFA was added to the reaction mixture in order to stop the lysine-C digestion, and then the reaction mixture was analyzed with a MALDI-TOF mass spectrometer.

Figure 2:
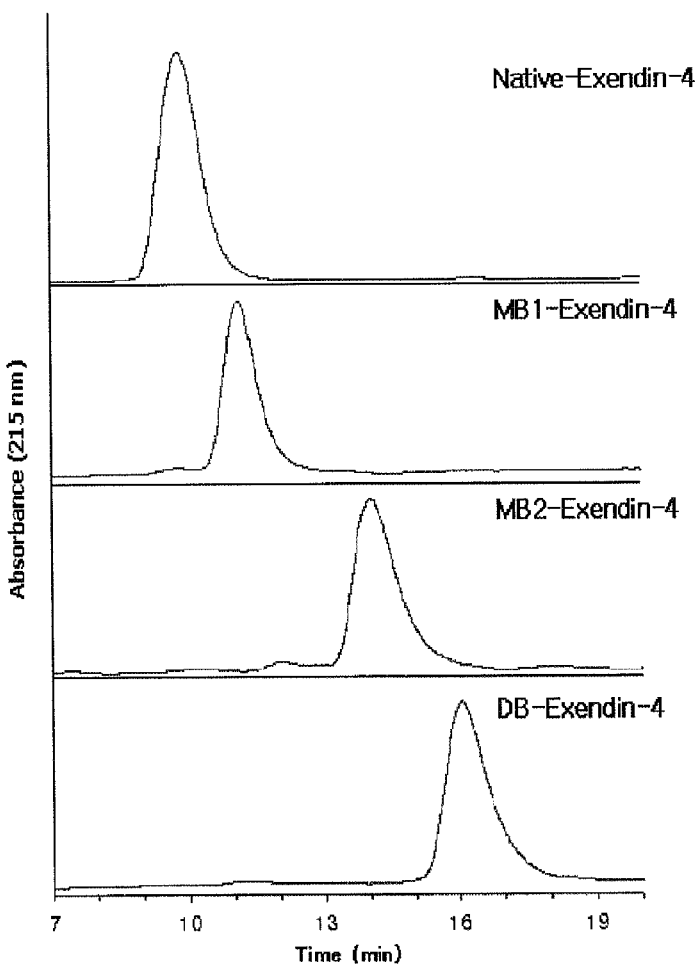
FIG. 2 shows HPLC chromatograms of exendin-4, MB1-exendin-4, MB2-exendin-4 and DB-exendin-4, separated from the mixture of FIG. 1.
Figure 3:
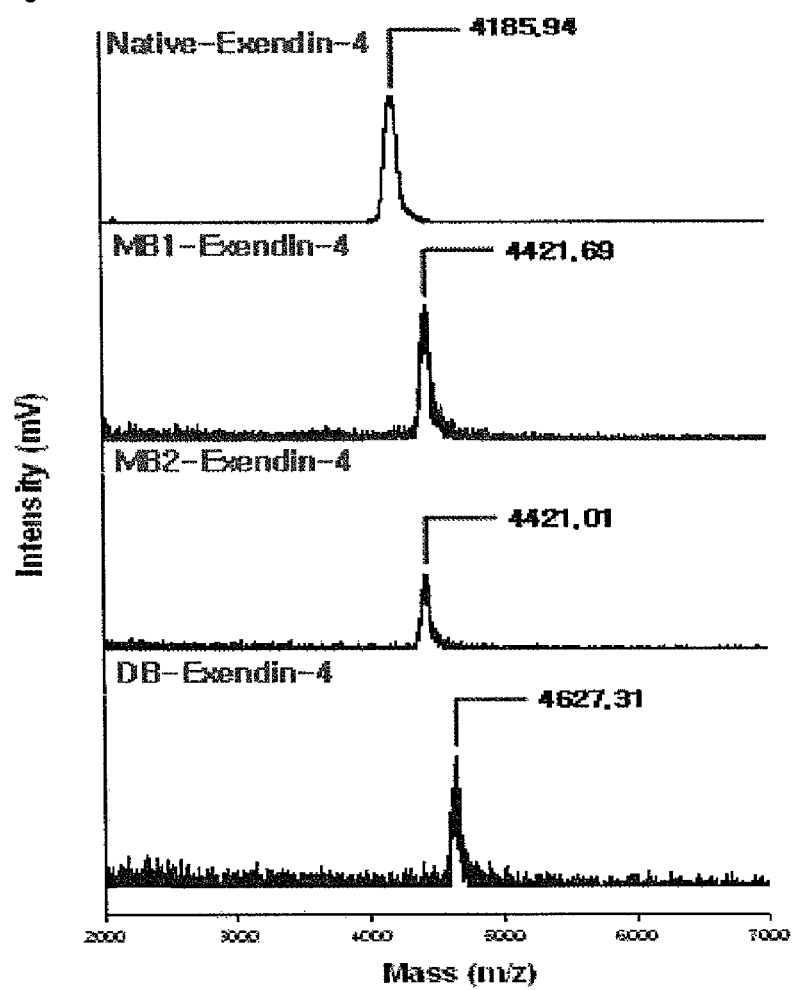
FIG. 3 shows the MALDI-TOF mass spectra of exendin-4, MB1-exendin-4, MB2-exendin-4 and DB-exendin-4 according to the present invention.

FIGS. 1 and 2 show an HPLC chromatogram of a mixture after completion of the reaction of biotin with exendin-4 and an HPLC chromatogram of modified exendin-4 finally separated from the mixture. Four different materials shown in FIG. 2 were separated from the reaction mixture. As shown in FIG. 3, it was found through MALDI-TOF mass spectrometry that the molecular weights of the separated materials were consistent with those of unreacted exendin-4, MB1-exendin-4, MB2-exendin-4 and DB-exendin-4, respectively. Also, the separated modified exendin-4 derivatives had a purity of more than 98%.

Figure 4:
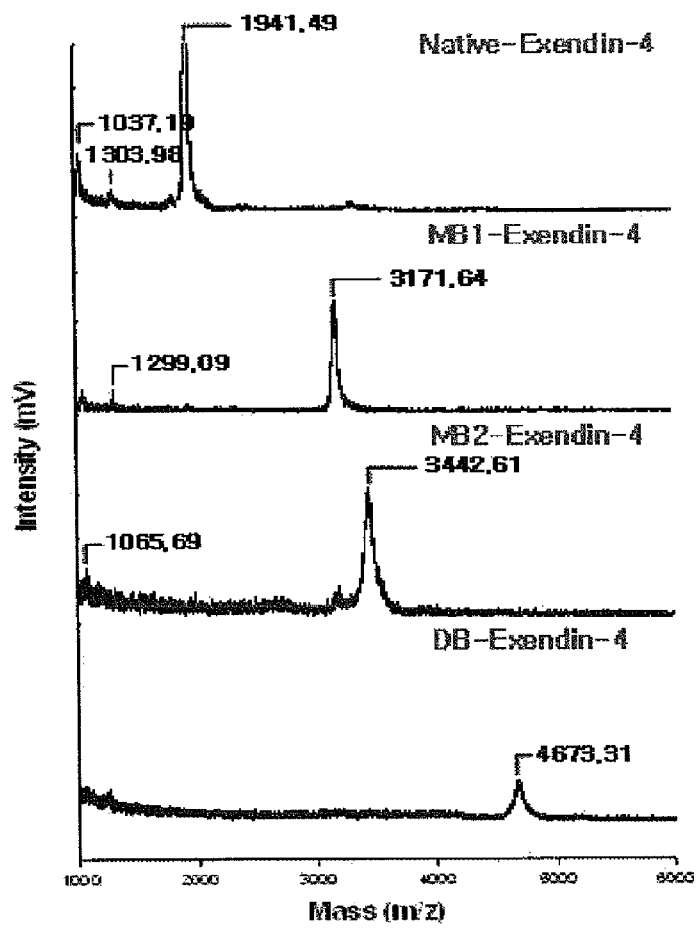
FIG. 4 shows the MALDI-TOF mass spectra of exendin-4, MB1-exendin-4, MB2-exendin-4 and DB-exendin-4 after enzymatic digestion with lysine-C.

The materials separated from the reaction mixture of biotin with exendin-4 were enzymatically digested with lysine-C, and then each of the reaction solutions was analyzed by MALDI-TOF mass spectrometry. The analysis results are shown in FIG. 4. As shown in FIG. 4, it was found that the materials were unreacted exendin-4, MB1-exendin-4, MB2-exendin-4 and DB-exendin-4, respectively.

Example 3

Analysis of Biological Stability of Exendin-4 Derivatives Modified with Biotin

The biological stability of the modified exendin-4 derivatives, prepared and separated in Examples 1 and 2, was performed through the analysis of time-residual amount using trypsin, which is an enzyme mainly degrading exendin-4, and an intestinal homogenate.

<3-1> Analysis of Stability of Biotin-Modified Exendin-4 Derivatives in Trypsin Enzyme 20 µl of each of exendin-4 and biotin-modified exendin-4 derivatives was added to 20 µl of 2 mM trypsin (25 mM phosphate buffer, pH 6.5) and then allowed to react in aqueous solution at 37° C. The reaction was stopped with 100 µl of 1% TFA-containing distilled water, and each reaction solution was analyzed using HPLC at varying points of time. The HPLC analysis was performed in the same manner as described in Example 2, and was carried out using a 36~42% solvent B as a mobile phase at a flow rate of 1 ml/min for 10 minutes.

Figure 5:
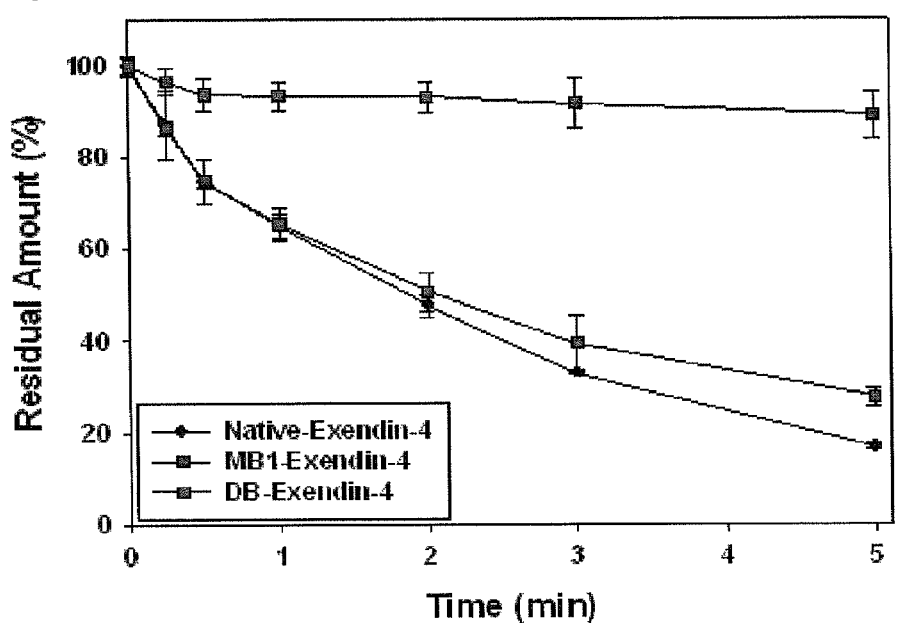
FIG. 5 shows the results of analysis of time-residual amount of exendin-4 and biotin-modified exendin-4 in trypsin enzyme.

FIG. 5 shows the results of analysis for the time-residual amount of exendin-4 and biotin-modified exendin-4 derivatives in trypsin enzyme. As shown in FIG. 5, DB-exendin-4 had significantly strong resistance to degradation in trypsin as compared to exendin-4. The results of analysis for the stability of biotin-modified exendin-4 derivatives in trypsin enzyme are shown in Table 1 below. As shown in Table 1, the half-lives of exendin-4, MB-exendin-4 and DB-exendin-4 were 2.3 min, 2.7 min and 28.1 min, respectively, that is, the half-lives of MB-exendin-4 and DB-exendin-4 were 1.2 times and 12.2 times as high as exendin-4, respectively.

TABLE 1

| Stability in trypsin enzyme | | |
|---|---|---|
| Kind of GLP-1 | Half-life | Folds increase |
| Exendin-4 | 2.3 | — |
| MB-exendin-4 | 2.7 | 1.2 |
| DB-exendin-4 | 28.1 | 12.2 |

<3-2> Analysis of Stability of Biotin-Modified Exendin-4 Derivatives in Intestinal Homogenate Each of 20 µl of exendin-4 and biotin-modified exendin-4 derivatives was added to 20 µl of an intestinal homogenate, and then allowed in aqueous solution at 37° C. The reaction was stopped with 100 µl of 1% TFA-containing distilled water, and each reaction solution was analyzed using HPLC at varying points of time. The HPLC analysis was performed in the same manner as described in Example 2, and was carried out using a 36-45% solvent B as a mobile phase at a flow rate of 1 ml/min for 15 minutes.

Figure 6:
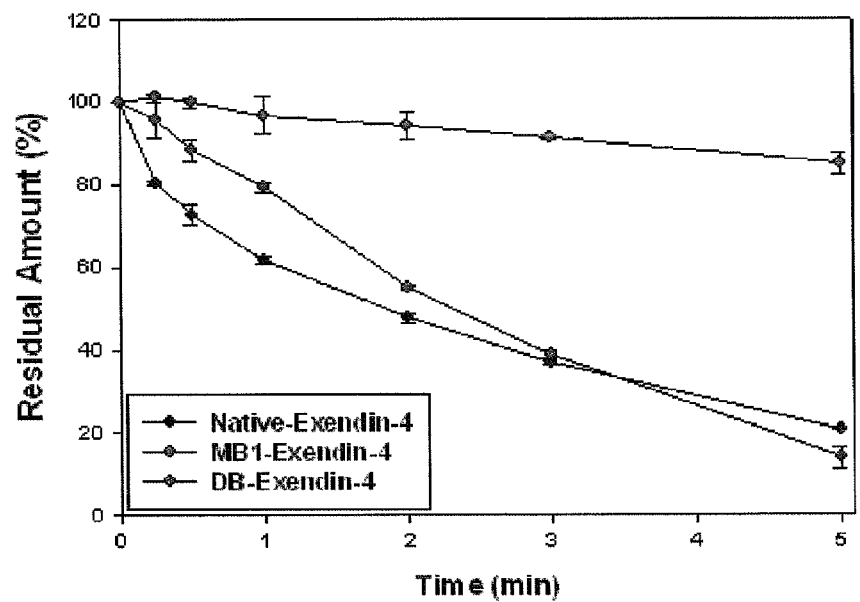
FIG. 6 shows the results of analysis of time-residual amount of exendin-4 and biotin-modified exendin-4 in intestinal juice.

FIG. 6 shows the results of analysis for the time-residual amount of exendin-4 and biotin-modified exendin-4 derivatives in intestinal homogenate. As shown in FIG. 6, it can be seen that DB-exendin-4 had significantly strong resistance to degradation in intestinal homogenate as compared to native exendin-4. The results of analysis for the stability of biotin-modified exendin-4 derivatives in intestinal homogenate are shown in Table 2 below. As can be seen in Table 2, the half-lives of exendin-4, MB-exendin-4 and DB-exendin-4 were 2.4 min, 2.7 min and 15.9 min, respectively, suggesting that the half-lives of MB-exendin-4 and DB-exendin-4 were 1.1-fold and 6.6-fold, respectively, higher than that of exendin-4.

TABLE 2

| Stability in intestinal homogenate | | |
|---|---|---|
| Kind of GLP-1 | Half-life | Folds increase |
| Exendin-4 | 2.4 | — |
| MB-exendin-4 | 2.7 | 1.1 |
| DB-exendin-4 | 15.9 | 6.6 |

Example 4

Measurement of Biological Activities of Biotin-Modified Exendin-4 Derivatives

The biological activities of position isomers of the biotin-modified exendin-4 derivatives, prepared and separated in Examples 1 and 2, were measured through an insulin secretion stimulating test using rat pancreatic islets and through receptor binding analysis using an insulin secreting cell line (INS-1 cell line).

<4-1> Insulin Secretion Stimulating Test

For an insulin secretion stimulating test, pancreatic islets were separated from laboratory rats (Sprague Dawley rats) by collagenase digestion and Ficoll density gradient separation. The separated pancreatic islets were cultured in a cell incubator for 2-3 days, and then placed in a 24-well plate, containing 1 ml of KRH buffer (containing 16.7 mM glucose), at a density of 20 islets/well. Then, each of exendin-4, MB-exendin-4 and DB-exendin-4 was added to the islets at varying concentrations of 0.1, 1, 10 and 100 nM, and the islets were cultured in a cell incubator for 2 hours. After completion of the culture, 200 µl of a culture sample was collected from the culture medium, and the concentration of insulin in the sample was measured using an insulin enzyme immunoassay kit.

Figure 7:
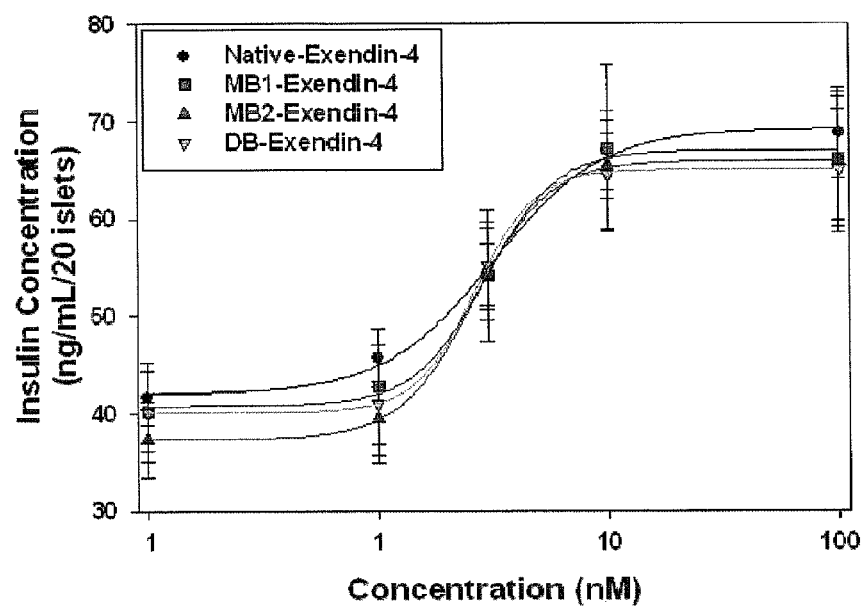
FIG. 7 shows the results of insulin secretion-stimulating tests of exendin-4 and biotin-modified exendin-4 in rat pancreatic islets.

FIG. 7 shows the results of insulin secretion stimulating tests of exendin-4, MB1-exendin-4, MB2-exendin-4 and DB-exendin-4. As shown in FIG. 7, it was observed that exendin-4, MB1-exendin-4, MB2-exendin-4 and DB-exendin-4 stimulated insulin secretion in a concentration-dependent manner. Such effects were stably increased in a concentration-dependent manner between exendin-4, MB1-exendin-4, MB2-exendin-4 and DB-exendin-4.

<4-2> Receptor Binding Test

The interaction of exendin-4 and biotin-modified exendin-4 derivatives with a GLP-1 receptor, the receptor of insulin-secreting cells, was analyzed through a receptor binding test. For the test, insulin-secreting INS-1 cells were placed in a 12-well plate at a concentration of $2.5 \times 10^5$ cells/well, and then cultured for 2 days, such that the cells stably adhered to the culture plate. After the cell adhesion, the culture medium was replaced with binding buffer, and $^{125}$I-exendin-4 (9-39)

was added thereto to a final concentration of 30 pM. Following this, each of exendin-4 and biotin-modified exendin-4 derivatives was added thereto to a final concentration of 0.001-100 nM, and then subjected to a competitive receptor binding assay at room temperature for 2 hours. After completion of the test, the cells were washed three times with cold phosphate buffer to remove unbound $^{125}$I-exendin-4. Finally, the cells were lysed with lysis buffer, the lysed cells were collected, and the amount of $^{125}$I-exendin-4 bound to the cells was measured using a gamma-ray spectrometer.

Figure 8:
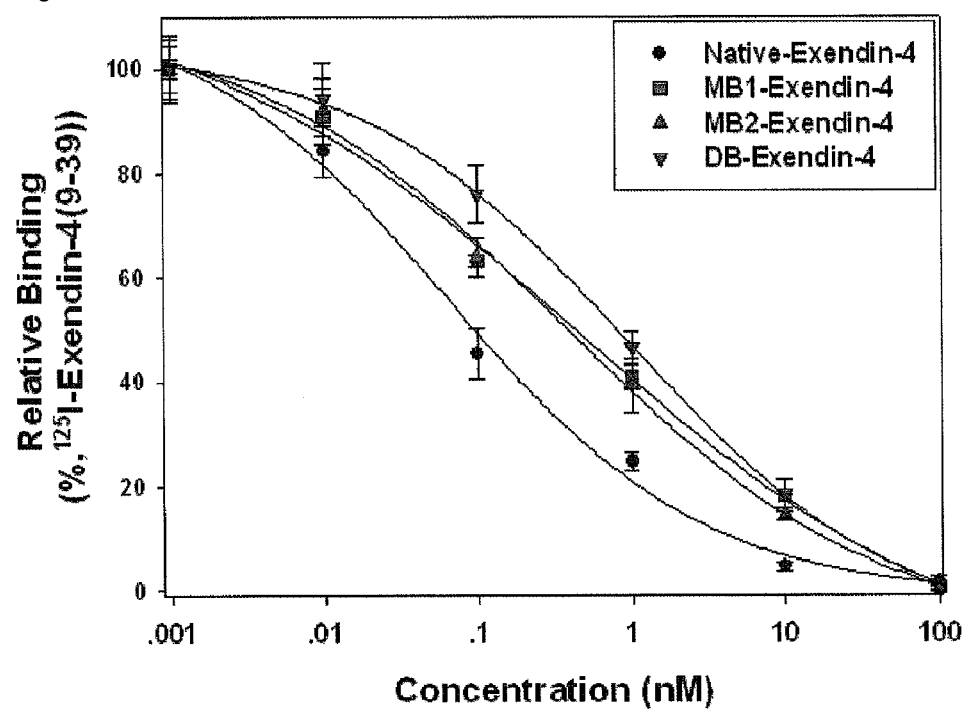
FIG. 8 shows the results of analysis for the receptor binding of exendin-4 and DB-exendin-4, analyzed using an insulin-secreting cell line (INS-1).

FIG. 8 shows the binding behavior of the insulin secreting cell surface with the GLP-1 receptor. As shown in FIG. 8, the competitive binding of $^{125}$I-exendin-4 was decreased with the increase in the concentration of the sample. Also, the position isomers showed a difference in binding strength according to the modification position. The EC50 (concentration upon the binding of 50% $^{125}$I-exendin-4) values of exendin-4, MB1-exendin-4, MB2-exendin-4 and DB-exendin-4, obtained through the test, were 0.9, 1.2, 1.8 and 1.5 nM, respectively.

Through such effects under cell culture conditions and the receptor binding tests, it can be seen that the receptor-binding abilities of the biotin-modified exendin-4 isomers were higher in the order of DB-exendin-4<MB2-exendin-4<MB1-exendin-4<exendin-4, but such difference was not attributable to the difference in the insulin secretion-stimulating ability as shown in FIG. 7. Accordingly, it could be seen that the biotin-modified exendin-4 derivatives had biological activity equal to that of native exendin-4.

Example 5

Measurement of Biological Activity of Biotin-Modified Exendin-4 Derivatives in Animal Model <5-1> Oral Glucose Tolerance Test in Animal Model In order to measure the oral glucose tolerance of exendin-4 and biotin-modified exendin-4 derivatives in an animal model, 6-week-old male db/db mice (C57/BLKS/J-db/db, Korea Research Institute of Bioscience and Biotechnology) were intraperitoneally injected with 100 μl of each of exendin-4 and biotin-modified exendin-4 derivatives (1 nmole/kg) at −30 min. Then, 200 μl of glucose (200 mg/ml) was orally administered to the mice, and at −30, 0, 15, 30, 60, 120 and 180 min, the change in the glucose level of the blood collected from the tail vein was observed.

Figure 9:
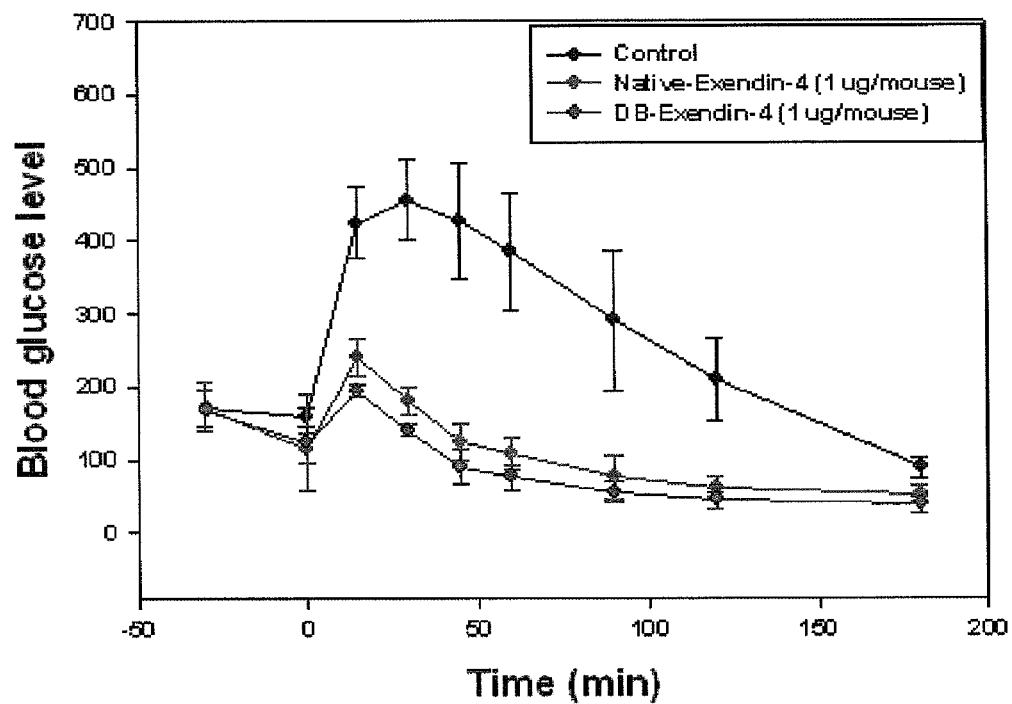
FIG. 9 is a graphic diagram showing the change in the blood glucose level of test animals, after exendin-4 and DB-exendin-4 were administered intraperitoneally to the animals.

As shown in FIG. 9, it could be seen that the groups administered with the drugs, and a control group (placebo, injected with saline), showed a significant difference in oral glucose tolerance. The control group showed a rapid increase in blood glucose level according to the administration of glucose and a slow lowering in blood glucose level. On the other hand, the groups administered with the drugs showed a relatively low increase in blood glucose level and a relatively rapid lowering in blood glucose level. A graphic diagram of the area under the glucose concentration curve between 0 min and 180 min, obtained on the basis of the results of FIG. 10, is shown.

Figure 10:
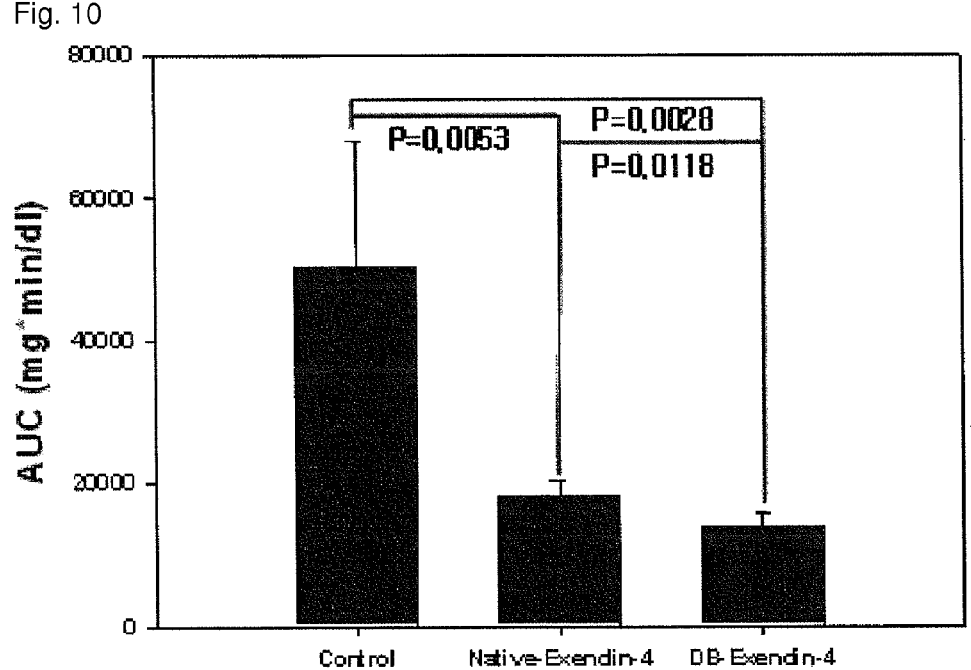
FIG. 10 shows the results of blood glucose lowering of exendin-4 and DB-exendin-4, obtained on the basis of the results of FIG. 9.

As shown in FIG. 10, the test group that was administered DB-exendin-4 or exendin-4 showed a very rapid blood-glucose removal ability compared to that of the control group (injected with saline). This is believed to be attributable to the increased insulin secreting ability of DB-exendin-4 or exendin-4 in pancreatic islets. Accordingly, it could be seen that DB-exendin-4 chemically modified with biotin showed biological activity equal to that of native exendin.

<5-2> Measurement of Intraperitoneal Glucose Tolerance Test in Animal Model

The absorption behavior and efficacy of biotin-modified exendin-4 derivatives after oral administration in an animal model were observed by examining the change in the intraperitoneal glucose tolerance in the animals.

In order to measure the intraperitoneal glucose tolerance of exendin-4 and biotin-modified exendin-4 derivatives in an animal models, 6-week-old male db/db mice (C57/BLKS/J-db/db, Korea Research Institute of Bioscience and Biotechnology) were orally administered with 100 μl of each of exendin-4 and DB-exendin-4 (1 mg/mouse, based on exendin-4) at −30. Then, the animals were intraperitoneally injected with 200 μl of glucose (200 mg/ml), and −30, 0, 15, 30, 60, 120 and 180 min, the change in the glucose level of the blood collected from the tail vein was observed.

Figure 11:
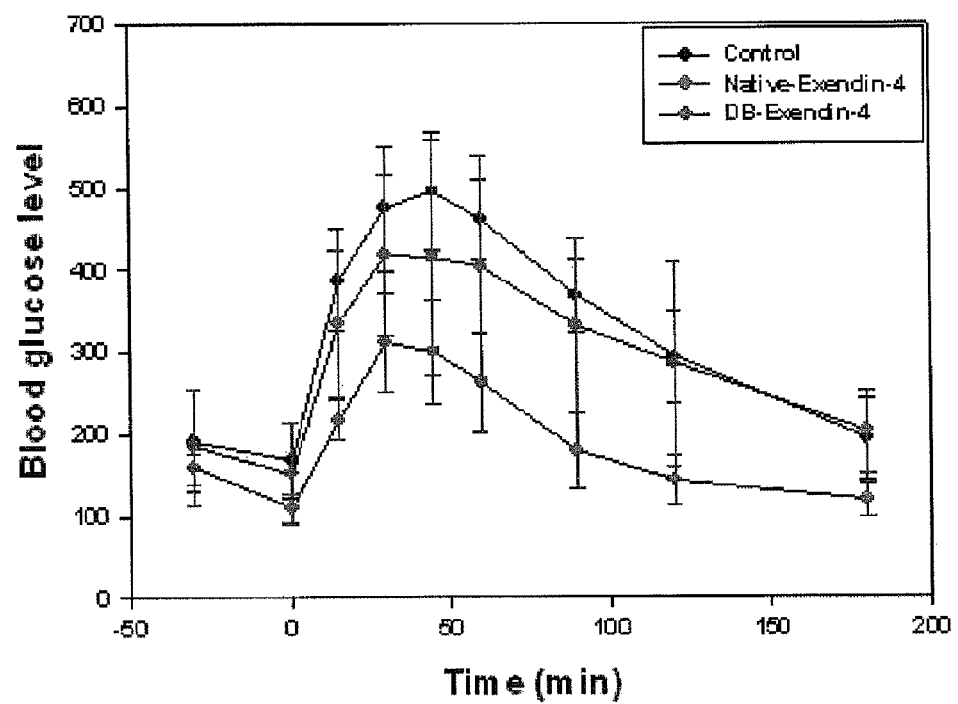
FIG. 11 is a graphic diagram showing the change in the blood glucose level of test animals, exendin-4 and DB-exendin-4 were administered orally to the animals.

As shown in FIG. 11, it could be seen that the groups administered with the drugs, and a control group (placebo, injected with saline), showed a significant difference in intraperitoneal glucose tolerance. The control group showed a rapid increase in blood glucose level according to the administration of glucose and a slow lowering in blood glucose level. However, the group administered with DB-exendin-4 showed a relatively slow increase in blood glucose level and a relatively rapid lowering in blood glucose level. Also, the group administered with native exendin-4 showed a slight increase in intraperitoneal glucose tolerance compared to the control group, but showed a decrease in intraperitoneal glucose tolerance compared to the group administered with DB-exendin-4. This is believed to be because the stabilization behavior and absorption of native exendin-4 and DB-exendin-4 in intestines are different between native exendin-4 and DB-exendin-4.

Figure 12:
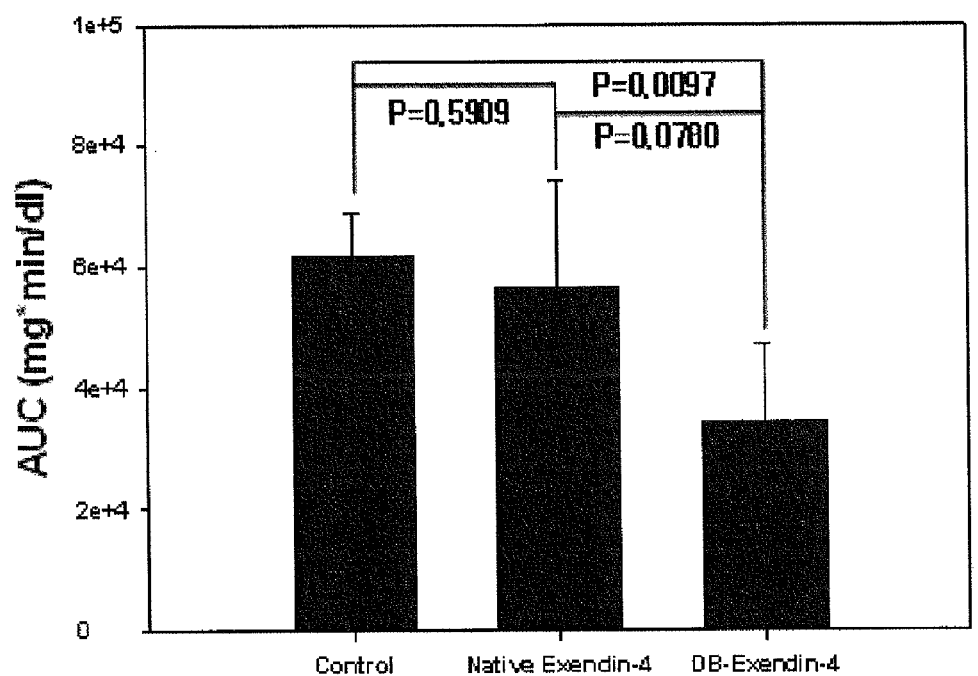
FIG. 12 shows the results of blood glucose lowering of exendin-4 and DB-exendin-4, obtained on the basis of the results of FIG. 11.

A graphic diagram of the area under the glucose concentration curve between 0 min and 180 min, obtained based on the results of FIG. 11, is shown in FIG. 12. As shown in FIG. 12, it could be seen that the intraperitoneal glucose tolerance was lower in the order of DB-exendin-4, exendin-4 and the control group. Also, this difference in efficacy is believed to be attributable to the difference in stability and absorption.

Through Example <5-2>, it could be seen that DB-exendin-4 when administered orally showed a more excellent anti-diabetic effect, that is, an increase in intraperitoneal glucose tolerance, compared to that of native exendin-4. To more closely examine this fact, the change in oral glucose tolerance according to the oral dosage of DB-exendin-4 was examined. In addition, in order to examine the difference between this changed glucose tolerance and the glucose tolerance in normal animals, the glucose tolerance in normal animals as a control group was examined.

<5-3> Examination of Efficacy According to Oral Dosage

This example was conducted in the same manner as described in Example <5-2>. Specifically, DB-exendin-4 was orally administered at dosages of 5, 1 and 0.2 mg/mouse at −30 min, 200 μl of glucose (200 mg/ml) was intraperitoneally injected, and at −30, 0, 15, 30, 60, 120 and 180 min, the change in the glucose level of the blood collected from the tail vein was observed. In the case of normal animals, the same dosage (relative to weight) of glucose as described above was administered, and then the change in blood glucose level was observed at the same points of time as described above.

Figure 13:
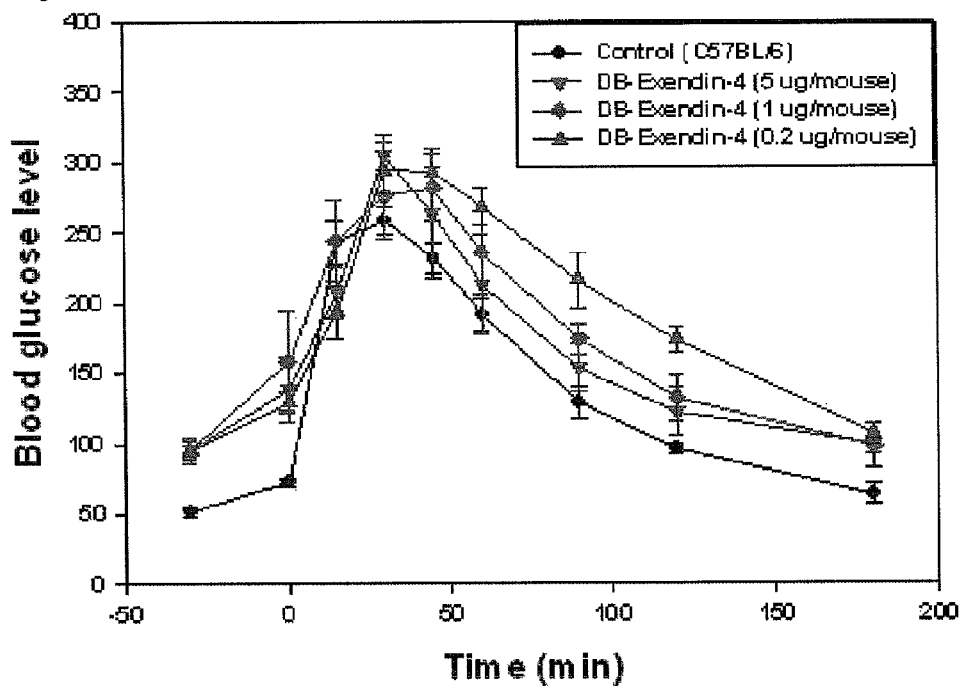
FIG. 13 is a graphic diagram showing the change in the blood glucose level of test animals after exendin-4 and DB-exendin-4 were administered orally to the animals in a concentration-dependent manner.

FIG. 13 shows the change in the intraperitoneal glucose tolerance of the animals, administered with varying dosages of DB-exendin-4, and in the intraperitoneal glucose tolerance of normal animals. It can be seen that the normal animals showed the most excellent glucose tolerance behavior and were restored to a normal blood glucose level at 120 min after the administration of glucose. However, the groups administered with DB-exendin-4 showed a slight increase in glucose tolerance with the increase in the dosage of DB-exendin-4. Also, the groups administered with DB-exendin-4 at dosages of 5 and 1 mg/mouse were restored to a normal blood glucose level at 2 hours, whereas the group administered with DB-exendin-4 at a dosage of 0.2 mg/mouse showed slightly reduced glucose tolerance and was maintained at a high blood glucose level, even at 2 hours after the administration of DB-exendin-4.

Figure 14:
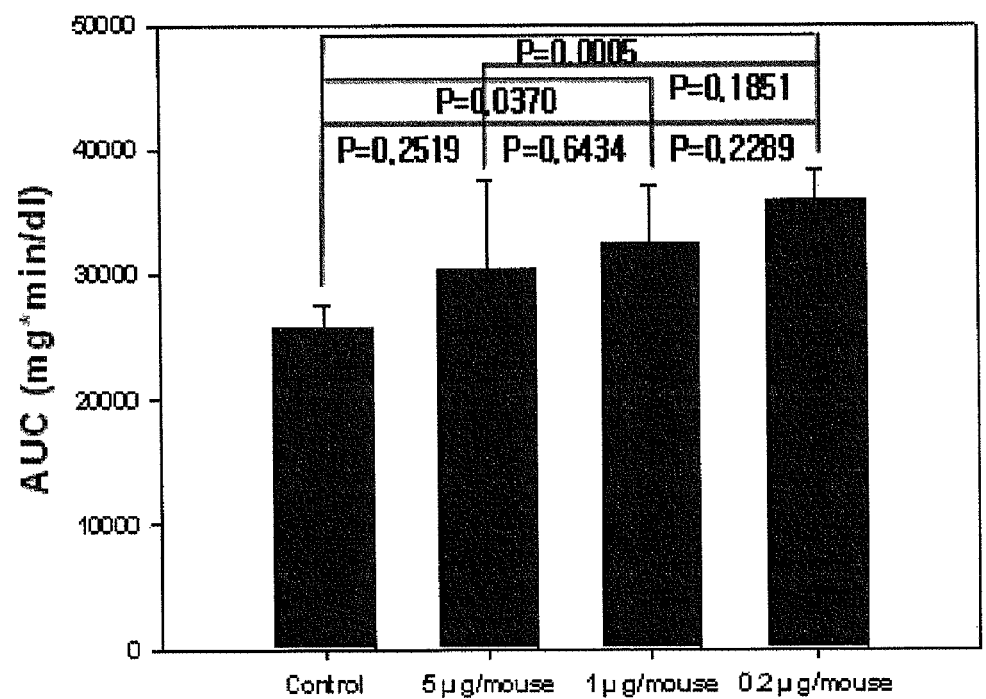
FIG. 14 shows the results of blood glucose lowering of exendin-4 and DB-exendin-4, obtained on the basis of the results of FIG. 13.

A graphic diagram of the area under the glucose concentration curve between 0 min and 180 min, obtained based on the results of FIG. 13, is shown in FIG. 14. As shown in FIG. 14, it could be seen that the groups administered with DB-exendin-4 showed a decrease in intraperitoneal glucose tolerance with the decrease in the dosage of DB-exendin-4.

Example 6

Examination of Pharmacokinetic Behavior of Exendin-4 Derivatives Modified with Biotin From the results of Examples 3-5 above, it was found that DB-exendin-4 of the present invention was excellent in biological stability, biological activity and blood glucose lowering effects in diabetic animals, and thus shows the characteristics of sustained drugs.

In order to examine the cause of such sustained characteristics, the pharmacokinetic behaviors of exendin-4 and DB-exendin-4 were observed. Laboratory rats (SD rats) weighing about 200 g were intravenously injected and orally administered with the drug at a dosage of 1 nmole/rat (10 μg/rat), and then the change in plasma blood drug concentration with time was measured using an ELISA kit. The plasma sample was collected from an inserted jugular vein catheter.

Figure 15:
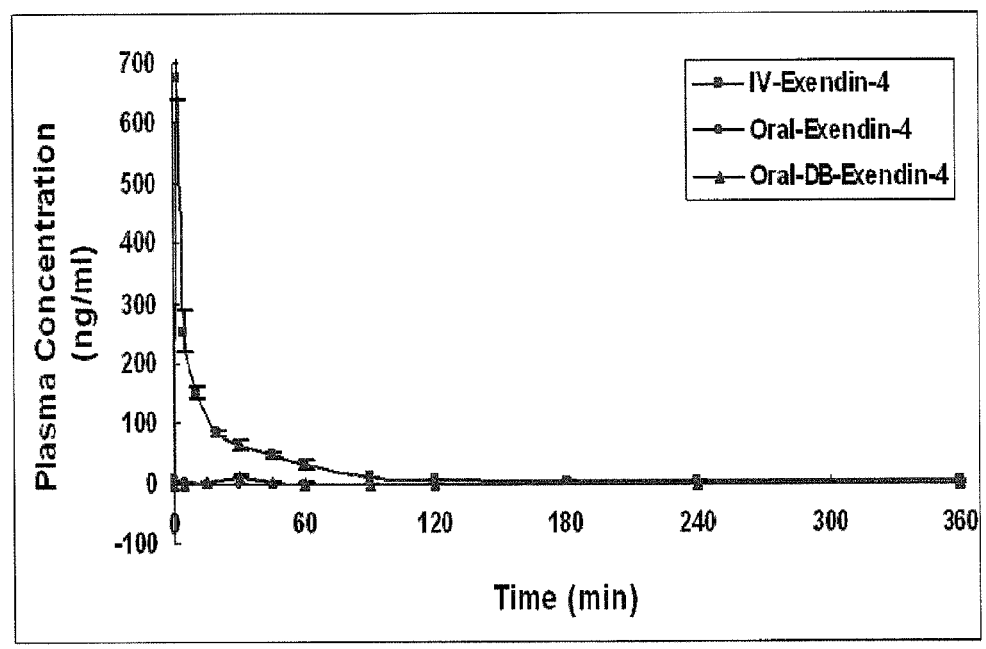
FIG. 15 shows the changes in blood concentration of exendin-4 and DB-exendin-4 after exendin-4 and DB-exendin-4 were intravenously injected and orally administered to rats.

The change in plasma drug concentration after the intravenous injection and oral administration of exendin-4 and DB-exendin-4 to the SD rats is shown in FIG. 15. As shown in FIG. 15, the DB-exendin-4 of the present invention reached the maximum plasma concentration at 15-30 min after oral administration, and then showed a slow decrease in the plasma concentration. However, exendin-4 showed a rapid decrease in the plasma concentration for a short time after intravenous injection and reached the basal concentration (<2 ng/ml) after 3 hours after intravenous injection. Also, it could be observed that there was no great change in the plasma concentration of exandin-4 after oral administration.

Figure 16:
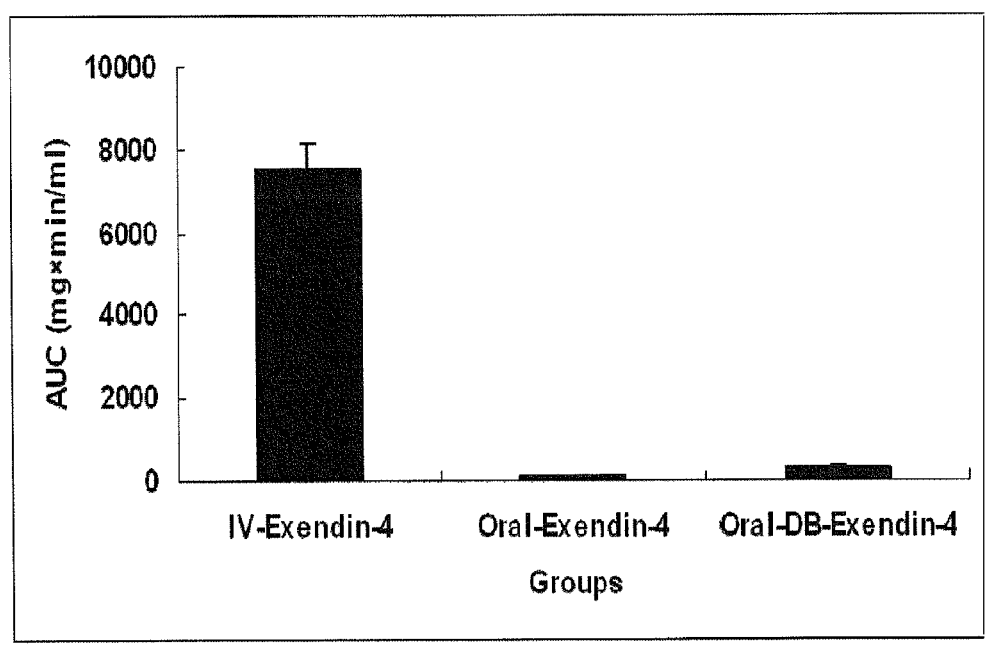
FIG. 16 is a graphic diagram showing the area under the blood concentration curve between 0 min and 180 min, obtained on the basis of the results of FIG. 15.

A graphic diagram of the area under the blood concentration curve between 0 min and 180 min, obtained based on the results of FIG. 15, is shown in FIG. 16. As shown in FIG. 16, it could be seen that the plasma concentration of DB-exendin-4 after oral administration reached 3.96% of the plasma concentration after intravenous injection of exendin-4. Accordingly, it could be found that DB-exendin-4 according to the present invention was effectively absorbed through oral administration, such that it could show effects.

Thus, from the results of Examples 3-6 above, it could be seen that exendin-4 chemically modified with biotin could have significantly increased stability through the bioconjugation process without reducing the activity of exendin and show improved anti-diabetic effects, resulting from excellent stability and absorption in intestines.

In addition, it could be seen that DB-exendin-4 showed a change in glucose tolerance through the regulation of dosage, that is, the organic relationship between dosage and efficacy, and could realize glucose tolerance in diabetic animals, similar to that in normal animals, through oral administration.

INDUSTRIAL APPLICABILITY

As can be seen from the foregoing, the present invention provides exendin derivatives modified with biotin, a method for preparing the same, and a pharmaceutical composition containing the biotin-modified exendin derivatives. The exendin-4 derivatives modified with biotin according to the present invention are useful for preventing or treating diseases such as diabetes or obesity, which are caused by the excessive secretion of insulin, or diseases such as irritable bowel syndrome, which are caused by the lowering of plasma glucose, the inhibition of gastric or intestinal mobility, the inhibition of gastric or intestinal emptying or the inhibition of food intake. Also, the exendin-4 derivatives modified with biotin can be applied as oral exendin preparations because most of exendin-related materials are currently developed as injection dosage forms, and agents for treating type II diabetes form a very large market.

The invention claimed is:

1. An exendin polypeptide linked to biotin, wherein the biotin is bound to at least one of lysine residue 12 and lysine residue 27 of exendin-4 having the amino acid sequence set forth in SEQ ID NO: 2.

2. The exendin polypeptide of claim 1, wherein the biotin is bound to lysine residue 12 and lysine residue 27 of exendin-4 having the amino acid sequence set forth in SEQ ID NO: 2.

3. A pharmaceutical composition for treating diabetes, which contains the exendin polypeptide of claim 1 as an active ingredient.

4. The pharmaceutical composition of claim 3, which is used to treat diabetes caused by excessive secretion of insulin.

5. The pharmaceutical composition of claim 3, wherein the diabetes is type II diabetes.

6. The pharmaceutical composition of claim 3, wherein the composition is formulated in the form of oral preparations, including tablets, pills, powders, granules, capsules, suspensions, solutions, emulsions or syrups, or parenteral preparations, including external preparations, suppositories or sterile injection solutions.

7. A pharmaceutical composition for treating obesity, which contains the exendin polypeptide of claim 1 as an active ingredient.

8. The pharmaceutical composition of claim 7, which is used to treat obesity induced by excessive secretion of insulin.

9. The pharmaceutical composition of claim 7, wherein the composition is formulated in the form of oral preparations, including tablets, pills, powders, granules, capsules, suspensions, solutions, emulsions or syrups, or parenteral preparations, including external preparations, suppositories or sterile injection solutions.

10. A pharmaceutical composition for treating irritable bowel syndromes, which contains the exendin polypeptide of claim 1 as an active ingredient.

11. The pharmaceutical composition of claim 10, which is used to treat irritable bowel syndromes, which are caused by lowering of plasma glucose, inhibition of gastric or intestinal motility, inhibition of gastric or intestinal emptying, or inhibition of food intake.

12. The pharmaceutical composition of claim 10, wherein the composition is formulated in the form of oral preparations, including tablets, pills, powders, granules, capsules, suspensions, solutions, emulsions or syrups, or parenteral preparations, including external preparations, suppositories or sterile injection solutions.

13. A method for preparing an exendin polypeptide linked to biotin, the method
comprising the steps of:
   i) adding exendin-4 having the amino acid sequence set forth in SEQ ID NO: 2, biotin and a reducing agent to a buffer or an organic solution, and allowing the mixture to react;
   ii) storing the reaction mixture of step i) at a given temperature for a given time in a light-shielded condition;
   iii) removing unreacted reactants from the reaction mixture of step ii); and
   iv) separating and purifying biotin-modified exendin from the product of step iii), from which the unreacted reactants have been removed.

14. The method of claim 13, wherein the biotin is bound to one or more of lysine residue 12 and lysine residue 27 of exendin 4.

15. The method of claim 13, wherein, in the step i), the reaction molar ratio of biotin to the exendin-4 having the amino acid sequence set forth in SEQ ID NO: 2 is in the range of 1-4.

* * * * *

SEQUENCE LISTING

<160> NUMBER OF SEQ ID NOS: 2

<210> SEQ ID NO 1
<211> LENGTH: 39
<212> TYPE: PRT
<213> ORGANISM: Heloderma horridum

<400> SEQUENCE: 1

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma suspectum

```
<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```